(12) United States Patent
Li et al.

(10) Patent No.: US 11,536,639 B2
(45) Date of Patent: Dec. 27, 2022

(54) INTELLIGENT LITHOLOGY IDENTIFICATION SYSTEM AND METHOD BASED ON IMAGES AND SPECTRUM TECHNOLOGY

(71) Applicant: SHANDONG UNIVERSITY, Shandong (CN)

(72) Inventors: Shucai Li, Jinan (CN); Zhenhao Xu, Jinan (CN); Heng Shi, Jinan (CN); Huihui Xie, Jinan (CN); Tengfei Yu, Jinan (CN); Wenyang Wang, Jinan (CN); Xin Huang, Jinan (CN); Yuchao Du, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 366 days.

(21) Appl. No.: 16/957,631

(22) PCT Filed: Apr. 26, 2019

(86) PCT No.: PCT/CN2019/084658
§ 371 (c)(1),
(2) Date: Jun. 24, 2020

(87) PCT Pub. No.: WO2020/199292
PCT Pub. Date: Oct. 8, 2020

(65) Prior Publication Data
US 2021/0215590 A1    Jul. 15, 2021

(30) Foreign Application Priority Data

Apr. 4, 2019   (CN) .......................... 2019102719271

(51) Int. Cl.
*G01N 15/02*   (2006.01)
*G01N 23/223*  (2006.01)
*G01N 23/207*  (2018.01)

(52) U.S. Cl.
CPC ..... *G01N 15/0205* (2013.01); *G01N 23/2076* (2013.01); *G01N 23/223* (2013.01); *G01N 2223/076* (2013.01)

(58) Field of Classification Search
CPC .. G01N 15/0205; G01N 23/223; G01N 23/20; G01N 23/2076; G01N 21/84;
(Continued)

(56) References Cited

U.S. PATENT DOCUMENTS 7,796,726 B1 *   9/2010   Gendreau .............. G01N 23/20
                                                        378/80
8,938,045 B2    1/2015   Dvorkin et al.
(Continued)

FOREIGN PATENT DOCUMENTS

CN    101718721 A    6/2010
CN    103376271 A    10/2013
(Continued)

OTHER PUBLICATIONS

Dec. 27, 2019 International Search Report issued in International Patent Application No. PCT/CN2019/084658.
(Continued)

*Primary Examiner* — Kiet T Nguyen
(74) *Attorney, Agent, or Firm* — Oliff PLC

(57) ABSTRACT

An intelligent lithology identification system and method based on images and spectrum technology. The intelligent lithology identification system includes a rock shape analysis system, an image identification system, a sample processing system, a spectrum analysis system, and a central analysis and control system; wherein the central analysis and control system determines the final lithology of a sample according to the rock identification results from the image identification system and the analysis results from the spectrum analysis system. The technical solution further identifies the content and type of minerals by using spectrum technology, integrates and analyzes the results of spectrum analysis and image identification, and finally gives the lithology of the rock, which greatly improves the accuracy of lithology identification.

10 Claims, 2 Drawing Sheets

(58) Field of Classification Search
CPC ........... G01N 33/24; G01N 2001/2866; G01N 2223/076; G01N 2223/1016; G01N 2223/616
USPC ...................................................... 376/237.1
See application file for complete search history.

(56) References Cited

U.S. PATENT DOCUMENTS

2019/0064039 A1* 2/2019 Ammar ................ G01N 33/241
2020/0182809 A1* 6/2020 Storer .................. G01N 23/207

FOREIGN PATENT DOCUMENTS

| CN | 104169714 A | 11/2014 |
| CN | 105241904 A | 1/2016 |
| CN | 108956674 A | 12/2018 |
| WO | 2016/205894 A1 | 12/2016 |

OTHER PUBLICATIONS

Dec. 27, 2019 Written Opinion issued in International Patent Application No. PCT/CN2019/084658.

* cited by examiner

INTELLIGENT LITHOLOGY IDENTIFICATION SYSTEM AND METHOD BASED ON IMAGES AND SPECTRUM TECHNOLOGY

FIELD OF THE INVENTION

The present disclosure relates to the technical field of rock identification and classification in engineering geology, in particular to an intelligent lithology identification system and method based on images and spectrum technology.

BACKGROUND OF THE INVENTION

Rock identification is a fundamental work in geological survey. During the field of geological survey, geologists may identify the lithology of rocks based on the color, the texture, the mineral composition and the like of rocks. With the rapid development of artificial intelligence (AI), more and more researchers have begun to identify the lithology of rocks using deep learning technology, and to analyze and process the image features of the rocks through intelligent algorithms such as machine learning, thereby reducing the dependence on professional knowledge and equipment, achieving the purpose of identifying the lithology of rocks from image identification, and effectively avoiding the problems of long time consumption, low accuracy and subjective influence in artificial identification of rocks.

However, the inventors found in research that with the wide application of image-based deep learning technology in lithology judgment, some problems have been gradually exposed. The determination of rock lithology should consider not only the appearance but also the composition and content of minerals, and these factors are often not reflected in the images. Therefore, when a variety of rock types are to be identified, it is unrealistic to rely simply on images to identify rock lithology.

SUMMARY OF THE INVENTION

One of the objectives of the embodiments of this description is to provide an intelligent lithology identification system based on images and spectrum technology, which integrates and analyzes the results of spectrum analysis and image identification to finally determine the rock lithology, thereby greatly improving the accuracy of rock lithology identification, and solving the problems of low accuracy and low efficiency in the existing lithology identification and classification.

An embodiment of this description provides an intelligent lithology identification system based on images and spectrum technology. The system is implemented by the following technical solution:

The system includes a rock shape analysis system, an image identification system, a sample processing system, a spectrum analysis system, and a central analysis and control system;

the rock shape analysis system acquires shape information of a sample to be tested, pre-selects a plurality of X-ray fluorescence (XRF) detection planes according to the shape information of the sample, determines a grinding position of the sample to be tested according to the grinding workloads of different detection planes, and transmits the grinding position of the sample to be tested and the flatness of the ground plane to the central analysis and control system;

the central analysis and control system controls, according to the determined grinding position of the sample to be tested, the sample processing system to grind the sample till meeting the requirement of XRF analysis for flatness, and the image identification system preliminarily identify the lithology of the ground rock;

the sample processing system grinds the debris produced in the grinding process of the sample after grinding the sample following the requirement of XRF analysis, and the image identification system judges whether the rock powder meets the requirement of X-ray diffraction analysis for the size of rock particles;

the spectrum analysis system performs X-ray diffraction (XRD) analysis on the rock powder meeting the requirement of particle size and XRF analysis on the rock sample meeting the requirement of sample flatness, and transmits respective analysis results to the central analysis and control system;

The central analysis and control system determines the final lithology of the sample according to the rock identification results from the image identification system and the analysis results from the spectrum analysis system.

The second objective of the embodiments of this description is to provide an intelligent lithology identification method based on images and spectrum technology, which integrates and analyzes the results of spectrum analysis and image identification to finally determine the rock lithology, thereby greatly improving the accuracy of rock lithology identification, and solving the problems of low accuracy and low efficiency in the existing lithology identification and classification.

Another embodiment of this description provides an intelligent lithology identification method based on images and spectrum technology. The method is implemented by the following technical solution:

The Method Includes:

acquiring shape information of a sample to be tested;

selecting an XRF detection plane according to the shape information of the rock, and determining a grinding position of the sample to be tested according to the detection plane;

grinding, after determining the grinding position of the sample to be tested, the sample till meeting the requirement of XRF analysis for flatness, and preliminarily identifying the lithology of the ground rock;

grinding, after grinding the sample to meet the requirement of XRF analysis for flatness, the debris produced in the grinding process of the sample, judging whether the ground rock powder meets the requirement of XRD analysis for the size of rock particles, and continuing to, if not meeting, grind the debris till meeting the requirement; and performing XRF analysis on the sample meeting the requirement of XRF analysis for flatness and XRD analysis on the rock powder meeting the requirement of XRD analysis for the size of rock particles respectively to obtain respective analysis results, and determining the final lithology of the sample according to the preliminary identification on the lithology of the rock and the two analysis results.

Compared with the prior art, the beneficial effects of the present disclosure are:

1. In the technical solution of the present disclosure, the sample is rotated by the retractable rotating grippers, the shape of the rock is detected by the laser rangefinders, an XRF detection position is pre-selected, the retractable rotating grippers grip the rock to move on the grinding member to grind the rock so as to form a plane for XRF detection, and the powder produced is used for XRD analysis.

2. The technical solution of the present disclosure uses rock identification based on deep learning twice, for detecting whether the rock powder meets the requirement of XRF analysis at the first time, and preliminarily identifying the lithology of the rock at the second time, thereby shortening the detection time and improving the work efficiency.

3. The technical solution of the present disclosure identifies the content and type of minerals by using spectrum technology, integrates and analyzes the results of spectrum analysis and image identification, and finally determines the lithology of the rock, which greatly improves the accuracy of lithology identification.

BRIEF DESCRIPTION OF THE DRAWINGS

The accompanying drawings constituting a part of the present disclosure are used for providing a further understanding of the present disclosure, and the schematic embodiments of the present disclosure and the descriptions thereof are used for interpreting the present disclosure, rather than constituting improper limitations to the present disclosure.

Figure 1:
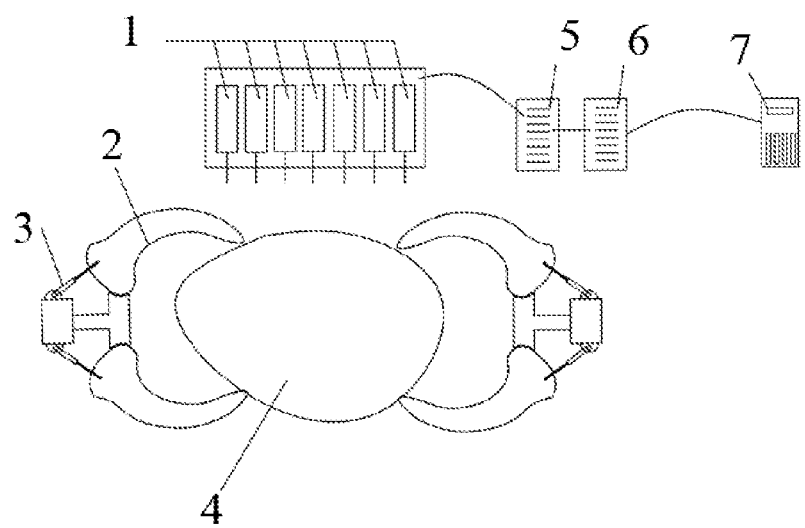
FIG. 1 is a schematic structural diagram of a rock shape generation system according to an embodiment of the present disclosure.

In which, 1, laser rangefinder; 2, clip; 3, first retractable member; 4, rock; 5, rock shape generation module; 6, rock XRF detection plane pre-selection module; 7, central analysis and control system; 8, first gear; 9, first drive motor; 10, second retractable member; 11, third retractable member; 12, fourth retractable member; 13, mobile base; 14, rail; 15, horizontal movement driving device; 16, grinding member; 17, support beam; 18, fifth retractable member; 19, second drive motor; 20, second gear; 21, clamping groove; 22, grinding stone; 23, rock debris; 24, grinding bowl; 25, XRF analyzer; 26, XRD analyzer; 27, second data processing unit; 28, camera; 29, rock particle detection model; 30, rock classification model; 31, third data processing unit.

DETAILED DESCRIPTION OF EMBODIMENTS

It should be noted that the following detailed descriptions are exemplary and are intended to provide further descriptions of the present disclosure. All technical and scientific terms used herein have the same meaning as commonly understood by those of ordinary skills in the technical filed to which the present disclosure belongs, unless otherwise indicated.

It should be noted that the terms used here are merely used for describing specific embodiments, but are not intended to limit the exemplary embodiments of the present invention. As used herein, unless otherwise clearly stated in the context, singular forms are also intended to include plural forms. In addition, it should also be understood that when the terms "comprise" and/or "include" are used in the description, it indicates the presence of features, steps, operations, devices, components, and/or combinations thereof.

Embodiment 1

This embodiment discloses an intelligent lithology identification system based on images and spectrum technology, including: a rock shape analysis system, an image identification system, a sample processing system, a spectrum analysis system, and a central analysis and control system; the rock shape analysis system acquires rock shape information and transmits the analysis result to the central analysis and control system; and the central analysis and control system controls, according to the analysis result transmitted by the rock shape analysis system, the sample processing system to process a sample.

The image identification system shoots rock debris, judges whether the size of rock debris particles meets the requirement of XRD for the size of rock debris particles, and transmits the result to the central analysis and control system, and the central analysis and control system controls, according to the result, the sample processing system to grind the rock debris again till the requirement is met. The image identification system shoots rock images and identifies the lithology of the rock sample.

The spectrum analysis system analyzes rock powder and the ground rock separately to obtain spectrum analysis results. The spectrum analysis system transmits the spectrum analysis results to the central analysis and control system; and the central analysis and control system fuses the results of rock image identification and spectrum analysis, and ultimately determines the lithology of the rock.

In an implementation example, the rock shape analysis system, as shown in FIG. 1, includes seven sets of laser rangefinders 1 or more; the laser rangefinders are above a sample to be tested, and a plurality of laser rangefinders point straight down and are on the same horizontal line. In this implementation example, the number and setting direction of the laser rangefinders adopt the above scheme in order to achieve accurate measurement of distances between the laser rangefinders and different positions of the sample to be tested below. When the sample is rotated in the space, the distances can be detected for different detection planes. Generally, because the planes of the sample to be tested are not flat planes, the distances between the different laser rangefinders and the different positions of the sample to be tested are different, and the shape information of the sample to be tested can be obtained by using the information of different distances.

During specific implementation, in order to obtain the distances between the different detection planes of the sample and the laser rangefinders, the sample needs to be rotated relative to the laser rangefinders. During the specific implementation, retractable rotating grippers are used to grip the rock to rotate uniformly under the laser rangefinders while the laser rangefinders transmit the information of distances between the rangefinders and the rock to a first data processing unit.

After that, the first data processing unit processes the received information. In which the first data processing unit includes a rock shape generation module 5 and a rock XRF detection plane pre-selection module 6. Specifically, the rock shape generation module is configured to generate rock shape information according to the information of distances between the different laser rangefinders and the rock, and the rock XRF detection plane pre-selection module 6 may preset several alternative grinding positions according to the rock shape information, then calculates the grinding workloads of the several alternative planes according to the rock shape information, and selects a preferred grinding position according to the grinding workloads. The first data processing unit can also calculate the flatness of the grinding plane of the sample to judge whether the flatness meets the requirement of XRF for plane detection; and the first data processing unit transmits, to the central analysis and control system 7, the information about whether the rock grinding position and the grinding plane meet the requirement for flatness.

In this implementation example, the interpretation corresponding to XRF is X-ray fluorescence spectrum analysis.

Figure 2:
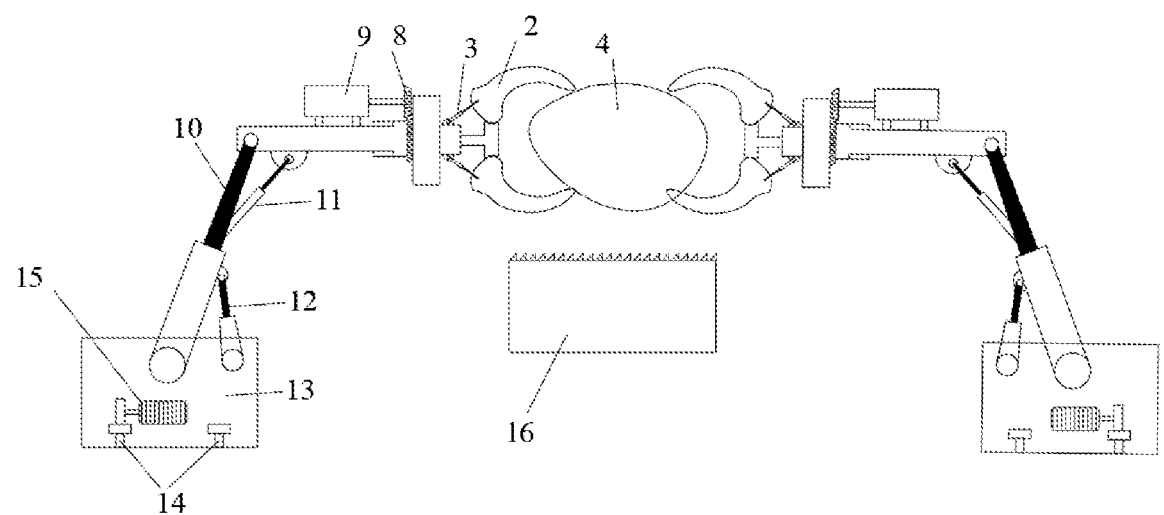
FIG. 2 is a schematic side view of part of a sample processing system according to an embodiment of the present disclosure.

In an implementation example, the sample processing system, as shown in FIG. 2, includes two retractable rotating grippers, horizontal guide rails, a grinding member and a grinding device. The retractable rotating gripper includes a clip and a first retractable member, and the clip 2 and the first retractable member 3 operate together to grip the sample; a first drive motor 9 and a first gear 8 operate together to drive the gripper and the rock to rotate within a vertical plane;

One end of a second retractable member 10 is fixed to a base of the drive motor and the other end is fixed to a mobile base 13, the middle portion of the second retractable member 10 is also connected to one end of a third retractable member 11 and one end of a fourth retractable member 12 respectively, the other end of the third retractable member 11 is fixed to the base of the drive motor, the second retractable member 10 and the third retractable member 11 are respectively fixed to different positions of the base of the drive motor, the other end of the fourth retractable member 12 is fixed to the mobile base 13, and the second retractable member 10 and the fourth retractable member 12 are respectively fixed to different positions of the mobile base 13. The second retractable member 10, the third retractable member 11, the fourth retractable member 12 and the first retractable member cooperate with each other to adjust the position of the rock gripped by the gripper.

A horizontal movement driving device 15 and rails 14 are also disposed on the mobile base 13. The horizontal movement driving device is connected to the central analysis and control system, the central analysis and control system controls the mobile base to operate, the horizontal movement driving device 15 includes a motor, and the motor operates under the control of the central analysis and control system to drive the mobile base to move horizontally.

The second retractable member 10 can extend and retract according to the actual situation to facilitate the control on the rotation of the rock; the mobile base 13 can play a role in supporting the entire rotating gripper, and can push the rotating gripper to slide along the rails 14 under the action of the horizontal movement driving device 15; the grinding member 16 is a hard strip-shaped stone block with fine diagonal lines on the surface, and the rotating grippers grip the sample to move horizontally on the grinding member under the push of the bases so as to quickly grind the test sample. The retractable rotating grippers can rotate within the vertical plane while gripping the sample; the retractable rotating grippers can move on the horizontal guide rails; the retractable rotating grippers can freely extend and retract; the two retractable rotating grippers are symmetrically arranged and operate together to grip the object; each of the two retractable rotating grippers is provided with retractable drive modules, a gripping drive module and a rotation drive module; and the retractable drive modules, the gripping drive module and the rotation drive module each is composed of a motor and a single-chip microcomputer.

Three retractable drive modules are provided, the three retractable drive modules control the extension and retraction of the second retractable member 10, the third retractable member 11 and the fourth retractable member 12 respectively, are connected to the central analysis and control system and receive control commands therefrom.

The gripping drive module is connected to the central analysis and control system, and can control the extension and retraction of the first retractable member 3, and in turn control the clip 2 to grip the test sample.

The rotation drive module is connected to the central analysis and control system. The first drive motor 9 rotates, the first gear 8 is driven to rotate, and the clip is in turn driven to grip the rock to rotate, wherein the rotation direction of the gear is opposite to that of the rock.

Figure 3:
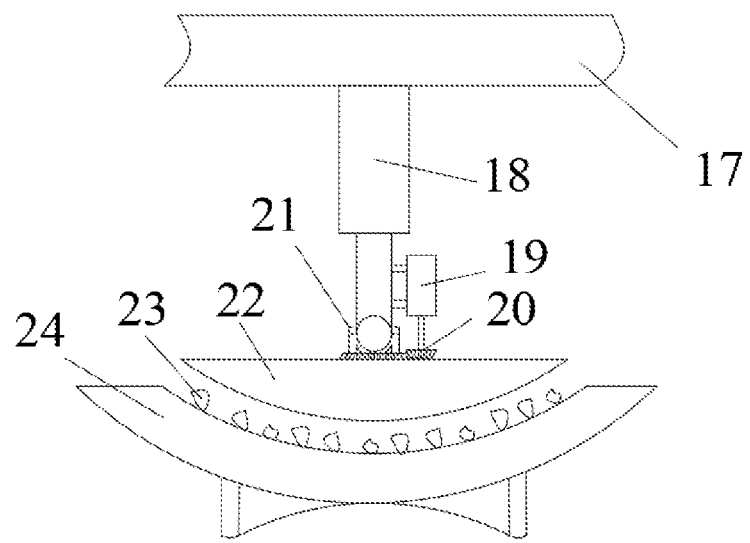
FIG. 3 is a schematic side view of an overall grinding according to an embodiment of the present disclosure.

In an implementation example, the mobile base is of a cuboid structure, and provides a supporting force for the upper structure to ensure the stability of the upper structure, and the rails control the moving direction of the grinding member as shown in FIG. 2. In an implementation example, the grinding device, as shown in FIG. 3, includes a support beam 17, a fifth retractable member 18, a second drive motor 19, a second gear 20, a clamping groove 21, and a grinding stone 22.

Specifically, the support beam 17 is fixedly connected to the fifth retractable member 18, one end of the fifth retractable member 18 is connected to the support beam 17 and the other end is spherically connected to the grinding stone. In the spherical connection, the other end of the fifth retractable member is a convex surface, the middle of the upper plane of the grinding stone 22 is a concave surface, and the convex surface fits the concave surface well to transmit force, while the fitting of the grinding stone 22 with a grinding bowl 24 is not affected by the inclination of the fifth retractable member 18.

The clamping groove 21 is disposed at the upper position on the round surface of the terminal of the fifth retractable member, and can transmit the pulling force to pull up the grinding stone 22 when the retractable member is stretched.

The fifth retractable member 18 is connected to the second drive motor 19, the second drive motor 19 is connected to the second gear 20, and the fifth retractable member and the second drive motor 19 are controlled by the central control unit.

In this implementation example, the grinding device is loaded by means of pressure control; the grinding stone in the grinding device is driven to rotate by the motor; the lower surface of the grinding stone and the upper surface of the grinding bowl have the same curvature, which can better ensure the grinding effect; the grinding stone in the grinding device is spherically connected to the fifth retractable member, which ensures that the grinding stone can still fit the grinding bowl well when the fifth retractable member is inclined to a certain extent; and the clamping groove 21 has the function of transmitting a tensile load, which ensures that the retractable member can suspend the grinding stone and the rock powder can be taken out smoothly.

The grinding device controls the load between the grinding stone and the rock particles by means of pressure control.

Figure 4:
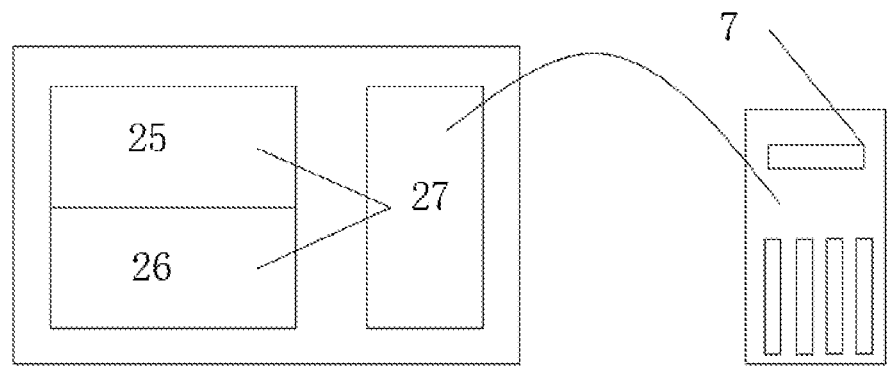
FIG. 4 is a schematic diagram of a spectrum analysis system according to an embodiment of the present disclosure.

In an implementation example, the spectrum analysis system, as shown in FIG. 4, includes an XRF analyzer 25 and an XRD analyzer 26; the XRF analyzer can identify the type and content of elements contained in the rock sample; the XRD analyzer can detect the type and content of minerals contained in the rock; a second data processing unit 27 integrates the diffraction analysis results and the fluorescence analysis results to verify and judge whether the errors of the detection results meet the requirements, thereby improving the accuracy of rock identification; and finally, the second data processing unit transmits the integration results to the central analysis and control system.

As the rock is named by additional modifiers and basic names, wherein the basic names reflect the basic characteristics of the rock and have certain mineral composition, mineral content, structure and structural characteristics. The additional modifiers are used to describe some important additional characteristics of the rock, and minor minerals, characteristic metamorphic minerals, structures, colors, etc., can be used as the additional modifiers. Image identification is used to determine the color, the structure and the structural characteristics, and spectrum analysis is used to determine the composition and content of minerals. The additional modifiers and the basic names complement each other to determine the name of the rock.

Figure 5:
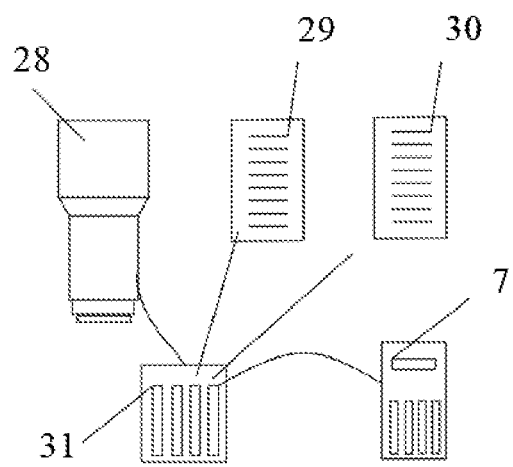
FIG. 5 is a schematic structural diagram of an image analysis system according to an embodiment of the present disclosure.

In an implementation example, the image identification system, as shown in FIG. 5, includes a camera 28, a rock particle detection model 29, a rock classification identification model 30, and a third data processing unit 31; the file corresponding to the rock particle detection model is a trained model file derived from other computer; the file corresponding to the rock classification identification model is a trained model file derived from other computer; the third data processing unit 31 judges, after reading a rock powder image and the rock particle detection model, whether the powder meets the requirement of XRD analysis for the size of rock particles; the third data processing unit 31 gives, after reading a rock image and the rock classification identification model, a preliminary identification on the lithology of the rock by calculation; and the third data processing unit 31 of the image identification system finally transmits the calculation result to the central analysis and control system 7. Specifically, the rock particle detection model 29 and the rock classification identification model 30 are stored in a memory unit, and the third data processing unit 31 calls the models stored in the memory unit when performing processing and judgment.

The central analysis and control system integrates the analysis results of the image identification system and the results of the spectrum analysis system to determine the final lithology. When the results do not conflict, the results can complement each other. When the results conflict, the results will be reported, and the research and development personnel can optimize the systems accordingly.

The identification system provided by the technical solution of the present disclosure can implement plane detection and grinding of a test rock, sample grinding, rock image acquisition, and spectrum analysis, thereby achieving intelligent identification of rock lithology; the method combines the deep learning technology for images and the existing spectrum technology, solves the problem of low accuracy of the existing methods relying on work experience, and can be widely used in the field of rock lithology identification and classification of geological engineering.

Embodiment 2

An intelligent lithology identification method based on images and spectrum technology according to this embodiment includes:

Step 1: a test rock is conveyed to the retractable rotating clips 2, the clips move below the laser rangefinders 1 under the action of the mobile bases 13, the first drive motors 9 drive the first gears 8 to rotate the rock 4 uniformly clockwise within the vertical plane, while the laser rangefinders 1 begin to measure distances in real time, the information of distances between the laser rangefinders and the rock is transmitted to the rock shape generation module 5 to generate a rock shape, the rock XRF detection plane pre-selection module 6 pre-constructs several detection planes for contrasting with the rock shape information to pre-select an XRF detection plane, in turn selects a corresponding grinding position on the surface of the test rock, and informs the central analysis and control system 7 of the selection result.

Step 2: the rotating grippers move the rock to the grinding member 16 under the command of the central control system for grinding, the rock shape is detected once at intervals to analyze whether the flatness of the ground plane meets the requirement of XRF analysis for flatness, the grinding status is reported to the central analysis and control system, and the central analysis and control system judges according to the grinding status whether to issue a grinding instruction to the sample processing system.

Step 3: when the ground plane meets the requirement of XRF analysis for flatness, the grinding device grinds rock debris and moves the rock powder to the image analysis system, the camera 28 shoots an image of the powder, the second data processing unit 31 reads the rock particle detection model 29 and the image to calculate and judge whether the rock powder meets the requirement of XRD analysis for the size of powder particles, and if not, the grinding continues till the requirement is met.

Step 4: the rock powder meeting the requirement is moved to the XRD analyzer 26 for XRD analysis, the ground rock is moved to the image identification system for shooting an image, and the third data processing unit 31 reads the rock classification model 30 and the image of the ground rock to identify the lithology; the ground rock is moved to the XRF analyzer 25, with the ground plane upward for convenient XRF spectrum analysis.

The spectrum analysis system performs XRD analysis on the rock powder, and transmits the analysis results to the central analysis system.

The rock is named by additional modifiers and basic names, wherein the basic names reflect the basic characteristics of the rock and have certain mineral composition, mineral content, structure and structural characteristics.

The additional modifiers are used to describe some important additional characteristics of the rock, and minor minerals, characteristic metamorphic minerals, structures, colors, etc., can be used as the additional modifiers.

Image identification (the results of rock image analysis) is used to determine the color, the texture and the structural characteristics, and spectrum analysis (the results of XRD analysis on the rock powder and the results of XRF analysis on the rock sample) is used to determine the composition and content of minerals. The additional modifiers and the basic name complement each other to determine the name of the rock.

XRF spectrum analysis is used to detect the type and content of elements, and XRD analysis is used to determine the composition and relative amount of minerals.

Whether the error between the two is within an acceptable range can be judged by comparing the results of the two, and if not, re-detection is required. This comparison can improve the accuracy of detection.

Step 5: the central analysis system compares and analyzes the rock identification results from the image identification system and the analysis results from the spectrum analysis system, and if the results are not inconsistent, the final name of the lithology is integrated according to the rock naming rule, otherwise, the errors are reported.

It could be appreciated that in this Description, the reference terms "an embodiment", "another embodiments", "other embodiments", or "the first embodiment to the N embodiment", etc., mean that specific features, structures, materials or characteristics described in conjunction with the embodiments or examples are included in at least one embodiment or example of the present invention. In this Description, the schematic descriptions of the above terms do not necessarily refer to the same embodiment or example. Moreover, the specific features, structures, materials or characteristics described may be combined appropriately in one or more embodiments or examples.

Described above are merely preferred embodiments of the present disclosure, and the present disclosure is not limited thereto. Various modifications and variations may be made to the present disclosure for those skilled in the art. Any modification, equivalent substitution, improvement or the like made within the spirit and principle of the present disclosure shall fall into the protection scope of the present disclosure.

The invention claimed is:

1. An intelligent lithology identification system based on images and spectrum technology, comprising:
   a rock shape analysis system, an image identification system, a sample processing system, a spectrum analysis system, and a central analysis and control system;
   the rock shape analysis system acquires shape information of a sample to be tested, pre-selects a plurality of X-ray fluorescence(XRF) detection planes according to the shape information of the sample, determines a grinding position of the sample to be tested according to grinding workloads of different detection planes, and transmits the grinding position of the sample to be tested and flatness of a ground plane to the central analysis and control system;
   the central analysis and control system controls, according to the determined grinding position of the sample to be tested, the sample processing system to grind the sample till meeting the requirement of XRF analysis for flatness, and the image identification system preliminarily identifies a lithology of a ground rock;
   the sample processing system grinds debris produced in the grinding process of the sample after grinding the sample following the requirement of XRF analysis, and the image identification system judges whether rock powder meets the requirement of X-ray diffraction (XRD) analysis for a size of rock particles;
   the spectrum analysis system performs XRD analysis on the rock powder meeting the requirement of particle size and XRF analysis on the rock sample meeting the requirement of sample flatness, and transmits respective analysis results to the central analysis and control system; the central analysis and control system determines the final lithology of the sample according to the rock identification results from the image identification system and the analysis results from the spectrum analysis system.

2. The intelligent lithology identification system based on images and spectrum technology according to claim 1, wherein the rock shape analysis system comprises a plurality of laser rangefinders, the laser rangefinders are above the sample to be tested, and the plurality of laser rangefinders point straight down and are on a same horizontal line.

3. The intelligent lithology identification system based on images and spectrum technology according to claim 2, wherein the rock shape analysis system further comprises a first data processing unit, and the laser rangefinders transmit information of distances between the rangefinders and the rock to the first data processing unit while the sample to be tested is rotated uniformly below the laser rangefinders;
   the first data processing unit comprises a rock shape generation module and a rock XRF detection plane pre-selection module;
   the rock shape generation module is configured to generate rock shape information according to the information of distances between the rangefinders and the rock;
   the rock XRF detection plane pre-selection module presets several alternative grinding positions according to the rock shape information, then calculates the grinding workloads of the several alternative planes according to the rock shape information, and selects a preferred grinding position according to the grinding workloads.

4. The intelligent lithology identification system based on images and spectrum technology according to claim 3, wherein the first data processing unit also calculates the flatness of a grinding plane of the sample to judge whether the flatness meets the requirement of XRF for plane detection; and the first data processing unit transmits, to the central analysis and control system, the information about whether the rock grinding position and the grinding plane meet the requirement for flatness.

5. The intelligent lithology identification system based on images and spectrum technology according to claim 1, wherein the sample processing system comprises two retractable rotating grippers arranged symmetrically relative to the sample to be tested, horizontal guide rails, a grinding member, and a grinding device;
   the retractable rotating grippers can rotate within a vertical plane while gripping the sample to be tested, the retractable rotating grippers gripping the sample can be pushed to slide along the rails under the action of a horizontal movement driving device, and then move horizontally on the grinding member, and the sample is quickly ground;
   the grinding device grinds a ground debris into powder.

6. The intelligent lithology identification system based on images and spectrum technology according to claim 5, wherein the grinding device comprises a support beam, a retractable member, a clamping groove, and a grinding stone;
   one end of the retractable member is connected to the support beam, and an other end of the retractable member is spherically connected to the grinding stone;
   the clamping groove is disposed at the upper position on a round surface of a terminal of the retractable member, and can transmit the pulling force to pull up the grinding stone when the retractable member is stretched.

7. The intelligent lithology identification system based on images and spectrum technology according to claim 6, wherein the grinding stone is driven to rotate by a motor; and a lower surface of the grinding stone and a upper surface of a grinding bowl have the same curvature.

8. The intelligent lithology identification system based on images and spectrum technology according to claim 1, wherein the spectrum analysis system comprises an XRF analyzer and an XRD analyzer; the XRF analyzer identifies the type and content of elements contained in the rock sample; the XRD analyzer detects the type and content of minerals contained in the rock; a second data processing unit integrates the diffraction analysis results and the fluorescence analysis results to verify and judge whether the errors of the detection results meet the requirements; and finally, the second data processing unit transmits the integration results to the central analysis and control system.

9. The intelligent lithology identification system based on images and spectrum technology according to claim 1, wherein the image identification system comprises a camera, a rock particle detection model, a rock classification identification model, and a third data processing unit; the third data processing unit judges, after reading a rock powder image and the rock particle detection model, whether the powder meets the requirement of XRD analysis for the size of rock particles; the third data processing unit gives, after reading a rock image and the rock classification identification model, a preliminary judgment on the lithology of the rock by calculation; and the third data processing unit of the image identification system finally transmits the calculation result to the central analysis and control system.

10. An intelligent lithology identification method based on images and spectrum technology, comprising:

acquiring shape information of a sample to be tested;

selecting an XRF detection plane according to the shape information of a rock, and determining a grinding position of the sample to be tested according to the detection plane;

grinding, after determining the grinding position of the sample to be tested, the sample till meeting the requirement of XRF analysis for flatness, and preliminarily identifying the lithology of a ground rock; grinding, after grinding the sample to meet the requirement of XRF analysis for flatness, a debris produced in the grinding process of the sample, judging whether a ground rock powder meets the requirement of XRD analysis for a size of rock particles, and continuing to, if not, grind the debris till meeting the requirement; and performing XRF analysis on the sample meeting the requirement of XRF analysis for flatness and XRD analysis on a rock powder meeting the requirement of XRD analysis for the size of rock particles respectively to obtain respective analysis results, and determining the final lithology of the sample according to the preliminary identification on the lithology of the rock and two analysis results.

\* \* \* \* \*